(12) United States Patent
Kimoto et al.

(10) Patent No.: US 8,128,555 B2
(45) Date of Patent: Mar. 6, 2012

(54) IN-VIVO INFORMATION ACQUIRING APPARATUS

(75) Inventors: Seiichiro Kimoto, Hachioji (JP); Takeshi Mori, Machida (JP)

(73) Assignees: Olympus Medical Systems Corp., Tokyo (JP); Olympus Corporation, Tokyo (JP)

(*) Notice: Subject to any disclaimer, the term of this patent is extended or adjusted under 35 U.S.C. 154(b) by 1278 days.

(21) Appl. No.: 11/825,245

(22) Filed: Jul. 5, 2007

(65) Prior Publication Data
US 2008/0009671 A1    Jan. 10, 2008

(30) Foreign Application Priority Data

Jul. 5, 2006  (JP) ................ 2006-185528

(51) Int. Cl.
*A61B 1/00* (2006.01)
*A61B 1/04* (2006.01)
(52) U.S. Cl. ........................................ 600/118
(58) Field of Classification Search .......... 600/103, 600/109, 117, 118, 160
See application file for complete search history.

(56) References Cited

U.S. PATENT DOCUMENTS

| | | | |
|---|---|---|---|
| 7,009,634 B2 | 3/2006 | Iddan et al. | |
| 2004/0087832 A1* | 5/2004 | Glukhovsky et al. | 600/118 |
| 2004/0254455 A1* | 12/2004 | Iddan | 600/424 |
| 2005/0054897 A1* | 3/2005 | Hashimoto et al. | 600/118 |
| 2005/0272973 A1* | 12/2005 | Kawano et al. | 600/102 |
| 2006/0241578 A1* | 10/2006 | Honda | 606/32 |
| 2009/0192353 A1* | 7/2009 | Segawa | 600/118 |

FOREIGN PATENT DOCUMENTS

| | | |
|---|---|---|
| EP | 1 510 169 | 3/2005 |
| GB | 2 320 630 | 6/1998 |
| JP | 62-115344 | 5/1987 |
| JP | 04-361422 | 12/1992 |
| JP | 08-005936 | 1/1996 |
| JP | 2000-156734 | 6/2000 |
| JP | 2003-523795 | 8/2003 |
| JP | 2004-261240 | 9/2004 |
| JP | 2005-073887 | 3/2005 |
| JP | 2005-081005 | 3/2005 |
| JP | 2005-237460 | 9/2005 |
| JP | 2006-094933 | 4/2006 |
| WO | WO 01/35813 A1 | 5/2001 |

OTHER PUBLICATIONS

English abstract only of International Publication No. WO 01/35813 A1.

* cited by examiner

*Primary Examiner* — Philip R Smith
(74) *Attorney, Agent, or Firm* — Scully, Scott, Murphy & Presser, P.C.

(57) ABSTRACT

An in-vivo information acquiring apparatus includes an information acquiring unit that acquires in-vivo information, a transmitting unit that transmits the in-vivo information to an outside of a living body, a power source that serves to supply power to the information acquiring unit and the transmitting unit, a power supply unit that is provided between the power source and at least one of the information acquiring unit and the transmitting unit so as to supply the power of the power source to at least one of the information acquiring unit and the transmitting unit, an external signal detecting unit that detects an external control signal supplied from outside and generates a control signal according to a detected state of the external control signal, a power supply controller that controls a power supply state of the power supply unit according to the control signal supplied from the external signal detecting unit, and a masking unit that masks the control signal supplied to the power supply controller by the external signal detecting unit for a predetermined time period.

16 Claims, 12 Drawing Sheets

IN-VIVO INFORMATION ACQUIRING APPARATUS

CROSS-REFERENCE TO RELATED APPLICATIONS

This application is based upon and claims the benefit of priority from Japanese Patent Application No. 2006-185528, filed Jul. 5, 2006, the entire contents of which are incorporated herein by reference.

BACKGROUND OF THE INVENTION

1. Field of the Invention

The present invention relates to an in-vivo information acquiring apparatus which acquires in-vivo information of an inside of a living body and transmits the in-vivo information to an outside of the living body.

2. Description of the Related Art

In recent years, a swallowable capsule endoscope is proposed in a field of endoscope. The capsule endoscope has an imaging function and a radio communication function. After being swallowed by a subject from the mouth for an observation (examination), the capsule endoscope travels through body cavities, for example, inside internal organs such as a stomach and a small intestine following peristaltic movements thereof until being naturally excreted. The capsule endoscope has a function of capturing an intra-subject image, for example, every 0.5 second during the travel.

While traveling through the body cavities, the capsule endoscope sequentially transmits image data acquired through image-pickup inside the body of the subject to the outside by radio communication. The transmitted image data is stored in a memory outside the body of the subject. The subject can move freely after swallowing the capsule endoscope until excreting the same by carrying a receiver which is equipped with a radio communication function and a memory function. After the subject excretes the capsule endoscope, a doctor or a nurse can make diagnosis looking at images of organs presented on a display based on the image data stored in the memory (see, for example, International Publication WO 01/35813).

Most of the capsule endoscopes are configured to obtain driving power from an embedded power source. A configuration proposed for the control of the driving of the capsule endoscope includes a reed switch which is provided inside the capsule endoscope and turned on and off in response to an external magnetic field, and a permanent magnet which is provided in a package housing the capsule endoscope to supply the magnetic field. The reed switch in such a capsule endoscope is configured to maintain an off-state while an external magnetic field of a predetermined level or a higher level of intensity is supplied, and to be turned on when the intensity of the external magnetic field lowers. Therefore, while housed inside the package, the capsule endoscope is not driven; and once taken out from the package and away from the influence of the permanent magnet, the capsule endoscope starts to be driven. When the capsule endoscope has such a configuration, the driving of the capsule endoscope can be prevented as far as the capsule endoscope is housed inside the package (see International Publication WO 01/35813).

Further, another proposed capsule endoscope is configured so that power supply from a power source to function execution units such as an imaging unit is turned on and off according to toggle operations controlled according to external control signals such as a magnetic field generated by a magnet. In this case, the power supply from the power source can be turned on and off at any time even when the capsule endoscope is in the package as far as the capsule endoscope has not been introduced inside the subject, whereby unnecessary power consumption of the power source and unnecessary radiation of electric waves can be prevented (see Japanese Patent Application Laid-Open No. 2005-81005).

However, when a magnet is made to continuously move at high speed around the above-mentioned conventional capsule endoscope, which is turned on and off according to toggle operations, the interval of toggle operations shortens.

Hence, it is necessary to prevent the shortening of the interval of toggle operations, e.g., by preventing the high-speed movements of the magnet around the capsule endoscope, particularly when the capsule endoscope includes circuitry in which resetting of an internal circuit is necessary after the power is once turned off and turned on again, so that the time necessary for the resetting is secured.

Further, since the capsule endoscope in general has a limitation in the amount of mountable power supply, power consumption of stand-by circuits must be minimized.

SUMMARY OF THE INVENTION

An object of the present invention is at least to solve the problems as described above.

According to one aspect of the present invention, an in-vivo information acquiring apparatus includes an information acquiring unit that acquires in-vivo information, a transmitting unit that transmits the in-vivo information to an outside of a living body, a power source that serves to supply power to the information acquiring unit and the transmitting unit, a power supply unit that is provided between the power source and at least one of the information acquiring unit and the transmitting unit so as to supply the power of the power source to at least one of the information acquiring unit and the transmitting unit, an external signal detecting unit that detects an external control signal supplied from outside and generates a control signal according to a detected state of the external control signal, a power supply controller that controls a power supply state of the power supply unit according to the control signal supplied from the external signal detecting unit, and a masking unit that masks the control signal supplied to the power supply controller by the external signal detecting unit for a predetermined time period.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of an in-vivo information acquiring apparatus according to the present invention will be described below with reference to the accompanying drawings. It should be noted, however, that the present invention is not limited to the embodiments.

First Embodiment

Figure 1:
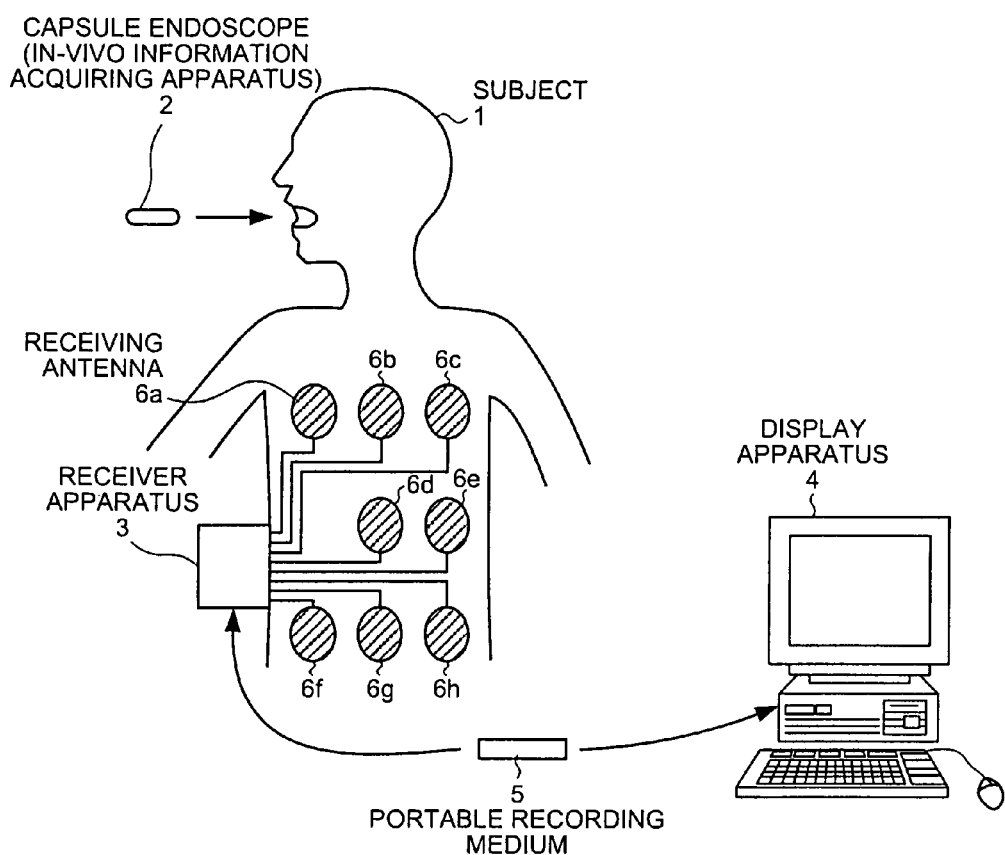
FIG. 1 shows an overall configuration of an in-vivo information acquiring system including an in-vivo information acquiring apparatus according to a first embodiment of the present invention.

An in-vivo information acquiring system according to a first embodiment of the present invention will be described. FIG. 1 is a schematic diagram of an overall configuration of the in-vivo information acquiring system according to the first embodiment of the present invention. As shown in FIG. 1, the in-vivo information acquiring system according to the first embodiment includes a capsule endoscope 2 which is an in-vivo information acquiring apparatus that is introduced inside a subject 1 and travels along a passage, a receiver apparatus 3 which receives radio signals including in-vivo information transmitted from the capsule endoscope 2, a display apparatus 4 which displays a content of the in-vivo information included in the radio signals received by the receiver apparatus 3, and a portable recording medium 5 which serves to deliver information between the receiver apparatus 3 and the display apparatus 4.

The display apparatus 4 serves to display, for example, the in-vivo images acquired through image-pickup by the capsule endoscope 2 and received by the receiver apparatus 3. The display apparatus 4 is configured like a workstation or the like that displays images based on data acquired from the portable recording medium 5. Specifically, the display apparatus 4 may be configured to directly display images and the like as in a Cathode Ray Tube (CRT) display or a liquid crystal display, or the display apparatus 4 may be configured to output images and the like to other medium as in a printer.

The portable recording medium 5 is attachable/detachable to/from the receiver apparatus 3 and the display apparatus 4. The portable recording medium 5 is configured so as to be able to output or record information when attached to the receiver apparatus 3 or the display apparatus 4. Specifically, while the capsule endoscope 2 travels through the body cavities of the subject 1, the portable recording medium 5 is attached to the receiver apparatus 3 to record in-vivo images. After the capsule endoscope 2 is excreted from the subject 1, the portable recording medium 5 is taken out from the receiver apparatus 3 and attached to the display apparatus 4, and the recorded data is read out by the display apparatus 4. When the data delivery between the receiver apparatus 3 and the display apparatus 4 is performed with the use of the portable recording medium 5 such as a compact Flash® memory, the subject 1 can move freely even while the capsule endoscope 2 is traveling inside the subject 1, dissimilar to a time when the receiver apparatus 3 and the display apparatus 4 are connected by a cable.

Receiving antennas 6a to 6h are formed, for example with a loop antenna. The loop antenna is fixed at a predetermined position of the subject 1. Specifically, the loop antenna is arranged near the passage taken by the capsule endoscope 2.

Figure 2:
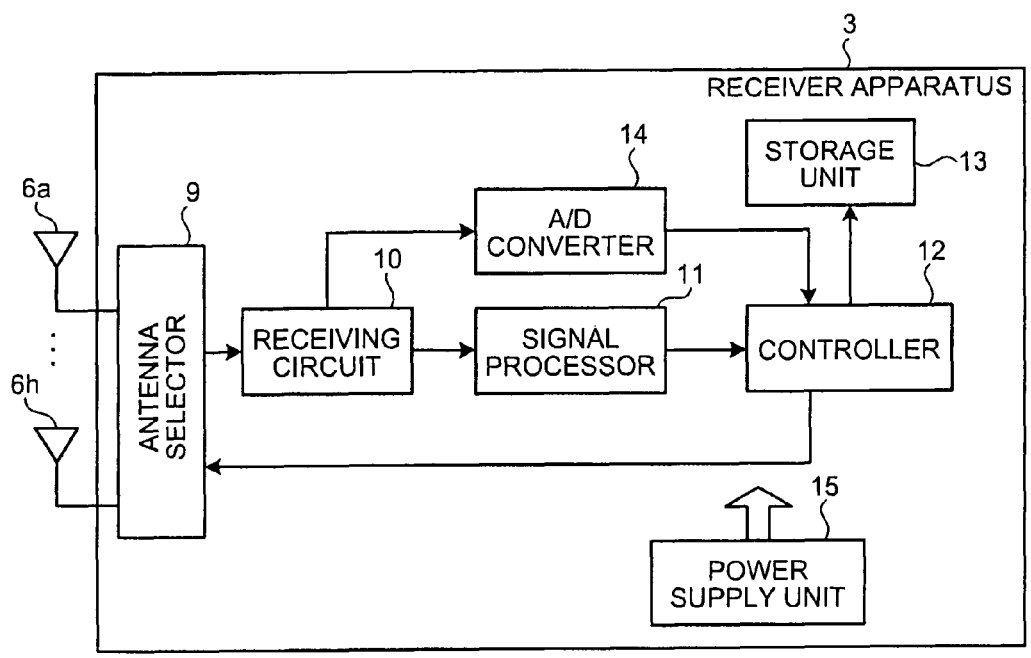
FIG. 2 is a block diagram of a configuration of a receiver apparatus shown in FIG. 1.

The receiver apparatus 3 serves to perform a reception process of the radio signals received via any one of the receiving antennas 6a to 6h. FIG. 2 is a block diagram of a configuration of the receiver apparatus 3. As shown in FIG. 2, the receiver apparatus 3 includes an antenna selector 9 that selects an appropriate receiving antenna for the reception of the radio signals from plural receiving antennas 6a to 6h, a receiving circuit 10 that performs processing such as demodulation of the radio signals received via the receiving antenna 6 selected by the antenna selector 9, and a signal processor 11 that serves to extract in-vivo images and the like from the processed radio signals. The receiver apparatus 3 further includes a controller 12 that performs a predetermined control related to an output, for example, of the extracted information, a storage unit 13 that stores the extracted information, an A/D converter 14 that performs A/D conversion of analog signals corresponding to the intensity of the radio signals supplied from the receiving circuit 10, and a power supply unit 15 that supplies driving power to each element.

The antenna selector 9 serves to select an appropriate receiving antenna for the reception of the radio signal from the plural receiving antennas 6a to 6h. Specifically, the antenna selector 9 has, for example, functions of selecting a receiving antenna which has a highest received electric-field strength under the control of the controller 12, and outputting the radio signals received via the selected receiving antenna 6 (hereinafter, reference character 6 denotes one of receiving antennas 6a to 6h) to the receiving circuit 10.

The receiving circuit 10 serves to perform predetermined processing such as demodulation on the radio signals received via the selected receiving antenna 6. Further, the receiving circuit 10 has a function of outputting an analog signal corresponding to the intensity of the radio signal to the A/D converter 14.

The signal processor 11 serves to extract predetermined information from signals subjected to the predetermined processing in the receiving circuit 10. For example, when the radio signals received by the receiver apparatus 3 are transmitted from an electronic device having an imaging function, the signal processor 11 extracts image data from the signals output from the receiving circuit 10.

The controller 12 serves to perform an overall control including an antenna selection operation of the antenna selector 9. Specifically, the controller 12 transfers the information output from the signal processor 11 to the storage unit 13 and makes the storage unit 13 store the information, and at the same time determines the receiving antenna 6 to be used based on the digital signal (such as Received Signal Strength Indicator (RSSI)) supplied from the A/D converter 14 corresponding to the reception intensity, and gives an instruction to the antenna selector 9.

The storage unit 13 serves to store the information extracted by the signal processor 11. Specifically, the storage unit 13 may be configured to store the information in a memory or the like provided in itself. In the first embodiment, however, the storage unit 13 is configured so as to have a function of writing the information into the portable recording medium 5 as described later.

The capsule endoscope 2 will be described. The capsule endoscope 2 serves as an example of the in-vivo information acquiring apparatus. The capsule endoscope 2 has functions of acquiring in-vivo information and transmitting radio signals including the acquired in-vivo information to the receiver apparatus 3.

Figure 3:
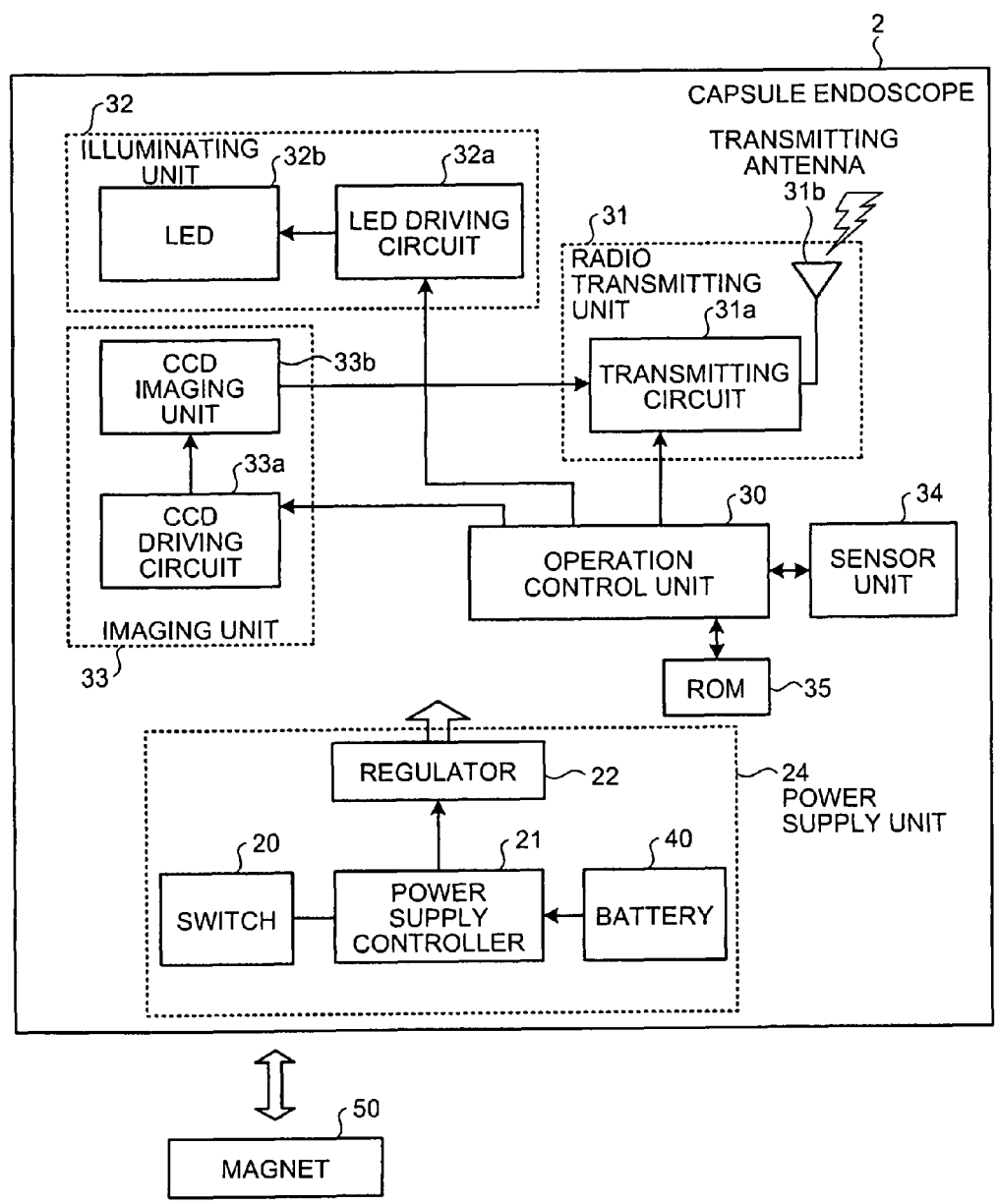
FIG. 3 is a block diagram of a configuration of a capsule endoscope shown in FIG. 1.

FIG. 3 is a block diagram schematically showing an incorporated structure of the capsule endoscope 2 inside an outer casing member. As shown in FIG. 3, the capsule endoscope 2 includes an imaging unit 33 that acquires in-vivo image information which is one type of the in-vivo information, an illuminating unit 32 that gives illumination at a time of image-pickup by the imaging unit 33, a sensor unit 34 that detects various physical values such as temperature, pressure, pH, and magnetism, a radio transmitting unit 31 that transmits information including the in-vivo information acquired by the imaging unit 33, the sensor unit 34, and the like by generating radio signals, an operation control unit 30 that controls an operation state of each of the above-described elements, a ROM 35 that stores and holds data such as programs and parameters employed in process control by the operation control unit 30, and a power supply unit 24 that supplies power to each element mentioned above.

The illuminating unit 32 includes an LED 32b that outputs illuminating light to irradiate the inside of the subject 1, and an LED driving circuit 32a that controls a driven state of the LED 32b. The imaging unit 33 includes a CCD imaging unit 33b that captures an image of at least a portion of an area illuminated by the LED 32b, converts the captured image into transmittable information and transmits the information to the radio transmitting unit 31, and a CCD driving circuit 33a that controls a driven state of the CCD imaging unit 33b.

The radio transmitting unit 31 includes a transmitting circuit 31a that performs generation and transmission of the radio signals including the in-vivo information output from the CCD imaging unit 33b and the operation control unit 30, and a transmitting antenna 31b that outputs the radio signals supplied from the transmitting circuit 31a to the outside as radio waves.

The power supply unit 24 includes a switch 20 that includes a reed switch which detects magnetism varied according to the approach and separation of an external magnet 50 and performs switching according to the intensity of the detected magnetism, a battery 40 that is realized with a button battery of silver oxide, for example, a power supply controller 21 that performs a conduction control of the power supplied from the battery 40 according to the on/off operations of the switch 20, a regulator 22 that converts the power supplied from the power supply controller 21 into power usable by each element. The power is supplied from the regulator 22 to each element inside the capsule endoscope 2.

Figure 4:
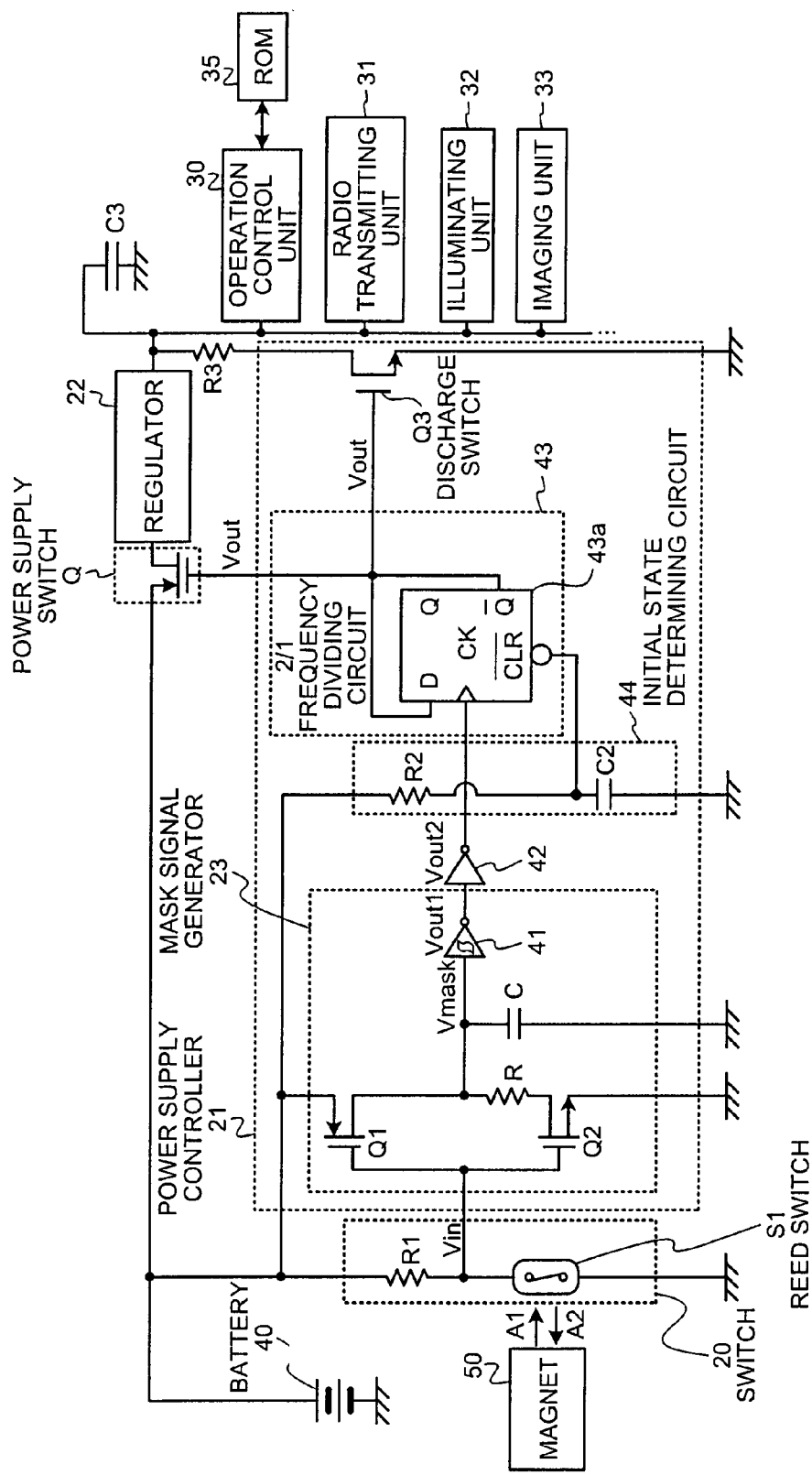
FIG. 4 is a circuit diagram of a detailed configuration of a power supply unit shown in FIG. 3.

Detailed configuration and operations of the power supply unit 24 will be described with reference to FIGS. 4 and 5. In FIG. 4, the power supply unit 24 includes, as described above, the battery 40, the switch 20, the power supply controller 21, and the regulator 22. Between the battery 40 and the regulator 22, a power supply switch Q is connected. The power supply switch Q is realized with p-MOS transistor. The power adjusted by the regulator 22 is supplied to the operation control unit 30, the radio transmitting unit 31, the illuminating unit 32, the imaging unit 33, and the like.

The switch 20 includes a resistor R1 and a reed switch S1 connected in series between a positive side of the battery 40 and the ground. The resistor R1 is connected to the side of the battery 40, whereas the reed switch S1 is connected to the side of the ground. When the magnet 50 is brought close to the reed switch S1 in a direction A1 from outside the capsule endoscope 2, the reed switch S1 is closed to attain a closed-state. On the other hand, when the magnet 50 is taken away from the reed switch S1 in a direction A2, the reed switch S1 is opened to attain an open-state. The reed switch S1 is a normally-open switch.

The power supply controller 21 includes a mask signal generator 23, a ½ frequency dividing circuit 43, an initial state determining circuit 44, and a discharge switch Q3. The power supply controller 21 is connected between the power supply switch Q and each of the battery 40 and the switch 20. A signal Vout supplied from the power supply controller 21 is applied to the gate of the power supply switch Q so as to control the power supply from the battery 40 to the regulator 22.

The mask signal generator 23 forms a complementary-type switching circuit including a p-MOS transistor Q1 and an n-MOS transistor Q2. Each of the gates of the p-MOS transistor Q1 and the n-MOS transistor Q2 receives a signal Vin supplied from a contact point of the resistor R1 and the reed switch S1. The source of the p-MOS transistor Q1 is connected to the battery 40, and the drain thereof is connected to the source of the n-MOS transistor Q2 via a resistor R. The drain of the n-MOS transistor Q2 is grounded. Further, a condenser C is connected to one side of the resistor R connected to the drain of the p-MOS transistor Q1. The other end of the condenser C is grounded. A signal Vmask supplied from one end of the condenser C is supplied to an inverter 41, which outputs an inverted version Vout1 of the Vmask.

In brief, the signal Vin which is an on/off switching signal corresponding to the operation of the reed switch S1 is supplied. When the reed switch is turned off, the signal Vin is supplied at the power supply level. Then, the p-MOS transistor Q1 is turned off and the n-MOS transistor Q2 is turned on. Therefore, the electric charges accumulated in the condenser C according to a time constant determined by the resistor R and the condenser C are gradually discharged, and the signal Vmask is supplied. On the other hand, when the reed switch S1 is on and the signal Vin is supplied at the ground level, the p-MOS transistor Q1 is turned on and the n-MOS transistor Q2 is turned off. Therefore, the condenser C is charged, and the signal Vmask is supplied as the power supply level. When the level of the signal Vmask becomes equal to or lower than a predetermined value Vth, the inverter 41 switches the signal Vout1 from the ground level to the power supply level. When the charge and the discharge of the condenser C are repeated and the signal Vmask does not attain the level equal to or lower than the Vth, such a period is a mask period during which a successive state change of the signal Vin is not accepted. In other words, the mask signal generator 23 is a pulse-width lengthening circuit which lengthens the pulse width of the signal Vin by a predetermined time period.

The signal Vout1 is supplied to the inverter 42, which inverts the supplied signal Vout1 into a signal Vout2, and supplies the Vout2 to the ½ frequency dividing circuit 43. The ½ frequency dividing circuit 43 performs frequency dividing of the signal Vout2 and applies the resulting signal Vout to the gate of the power supply switch Q as a final control on/off signal for the power supply switch Q. Since the power supply switch Q is a p-MOS transistor, the power supply switch Q is turned on when the Vout is of the ground level.

Conventionally, the toggle operation is for on/off of the reed switch S1. In the first embodiment, however, the toggle operations are performed for the on/off of the signal Vout1 or the signal Vout2 generated as a result the Vmask attains the predetermined value Vth once and returning to the original value.

A D-type flip flop circuit 43a may be a T-type flip flop circuit or other circuit that can perform ½ frequency dividing. Further, a clear terminal CLR of the D-type flip flop circuit 43a is connected to the initial state determining circuit 44 which includes a resistor R2 connected at the positive side of the battery 40 and a condenser C2 connected at the side of the ground. The on/off state of the power supply switch Q after the attachment of the battery 40 is determined by the initial state determining circuit 44. The resistor R2 and the condenser C2 can be omitted when the on/off state of the power supply switch Q after the attachment of the battery 40 is insignificant.

Figure 5:
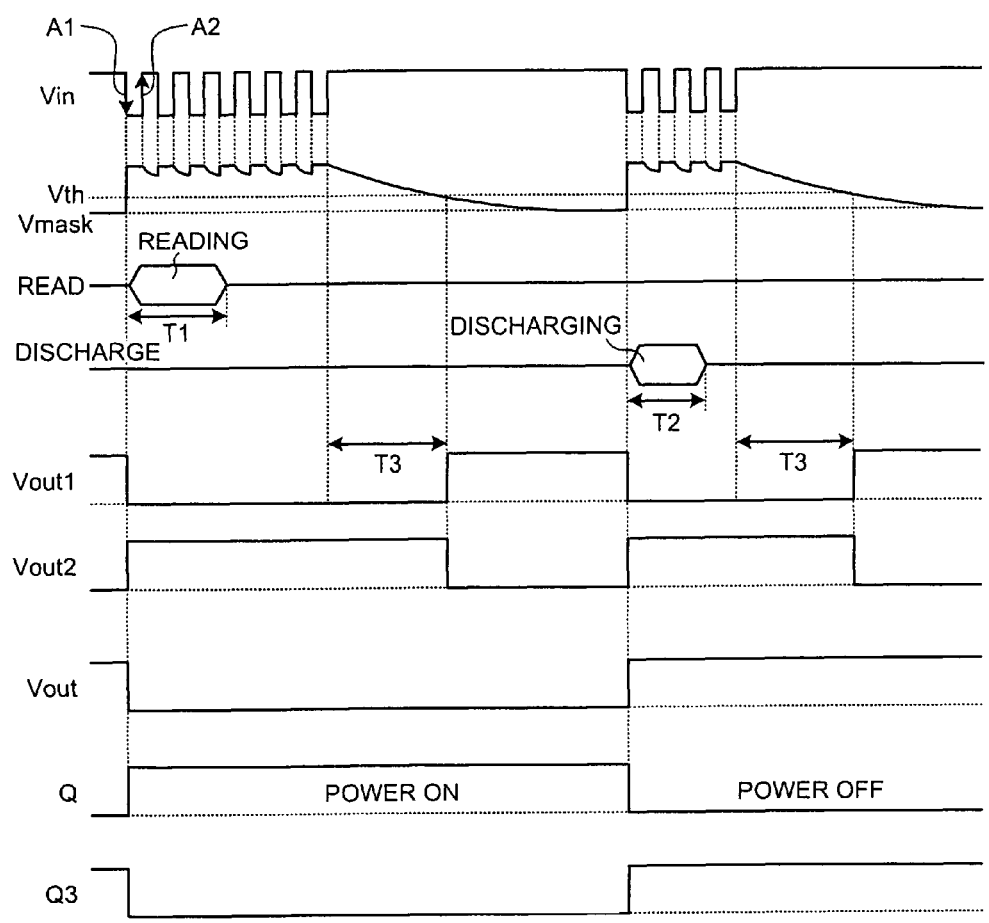
FIG. 5 is a timing chart of operations of a power supply controller shown in FIG. 4.

FIG. 5 is a timing chart of an example of on/off operations of the power supply switch Q. When the magnet 50 is made to move at high speed repetitiously so that the power supply switch Q is turned on for the transition to the power-on state, the signal Vmask rises sharply at the falling of the Vin. When the Vin rises, the Vmask gradually lowers according to the time constant CR. However, since the Vin falls before the Vmask lowers to the level of the predetermined value Vth, the Vmask maintains the level equal to or higher than the Vth. The values of the condenser C and the resistor R are determined to have such a time constant CR that the signal Vmask attains a level equal to or lower than the predetermined value Vth in a time period T3 after the pulse inputs of the signal Vin stop.

On the other hand, when the magnet 50 is made to move at high speed repetitiously so that the power supply switch Q is turned off for the transition to the power-off state, the Vmask sharply rises when the Vin falls similarly to the time of power-on. At the rising of the Vin, the Vmask gradually decreases according to the time constant of CR. However, since the Vin falls again before the Vmask falls to the level of the predetermined value Vth, the Vmask maintains the level equal to or higher than the Vth. The values of the condenser C and the resistor R are determined to have such a time constant CR that the signal Vmask attains a level equal to or lower than the predetermined value Vth in a time period T3 after the pulse inputs of the signal Vin stop. Since the condenser C and the resistor R are employed both at the time of power-on and power-off, the time T3 is equal at both times.

The time T3 is required to be a time period longer than a time period T1 which is required for the operation control unit 30 to read out the operation parameters stored in the ROM 35 on starting the operation control at the time of power-on. At the same time, T3 must be longer than a time period T2 which is a time required for the condenser C3 arranged to an output stage of the regulator 22 to have a sufficiently low voltage at the power-off time, in other words, for the electric charges accumulated in the condenser C3 to be sufficiently discharged.

When the mask time longer than the time T3 is secured, a time T1 for reading can be secured at the power-on time. Therefore, the reading out of the operation parameters is not intercepted, and the reliability of the operation control by the operation control unit 30 can be enhanced. Further, since the discharge time T2 is secured at the power-off time, even when the resettable voltage of the operation control unit 30 and the resettable voltage of the ROM 35 are different, the discharge of the condenser C3 is performed so that both the operation control unit 30 and the ROM 35 fall to the voltage equal to or lower than the resettable voltage. Therefore, malfunction caused by the presence of not-reset circuits can be prevented.

The discharge of electric charges starts in the condenser C3 as the power is turned off. The condenser C3 is a power supply condenser arranged to the output stage of the regulator 22, as described above. However, since the capsule endoscope 2 is designed to have a minimal leak current at the power-off time, the discharge time of the condenser C3 tends to be long. On the other hand, if the leak current of the condenser C3 is made large, the discharge time can be shortened. In this case, however, the battery is consumed even while the capsule endoscope 2 is turned off for storage, and a desirable operation of the capsule endoscope 2 may not be guaranteed.

Hence, in the first embodiment, the discharge switch Q3 is provided as an element realized with an n-MOS transistor arranged between the ground and the resistor R3 which has relatively low resistance and connected to the condenser C3. The signal Vout from the ½ frequency dividing circuit 43 is applied to the gate of the discharge switch Q3. Thus, the discharge switch Q3 attains an on-state during the power-off time as shown in FIG. 5, and the electric charges accumulated in the condenser C3 can be discharged in short time period through the resistor R3, whereby the reset operation can be performed stably and securely within a short time period.

Figure 6:
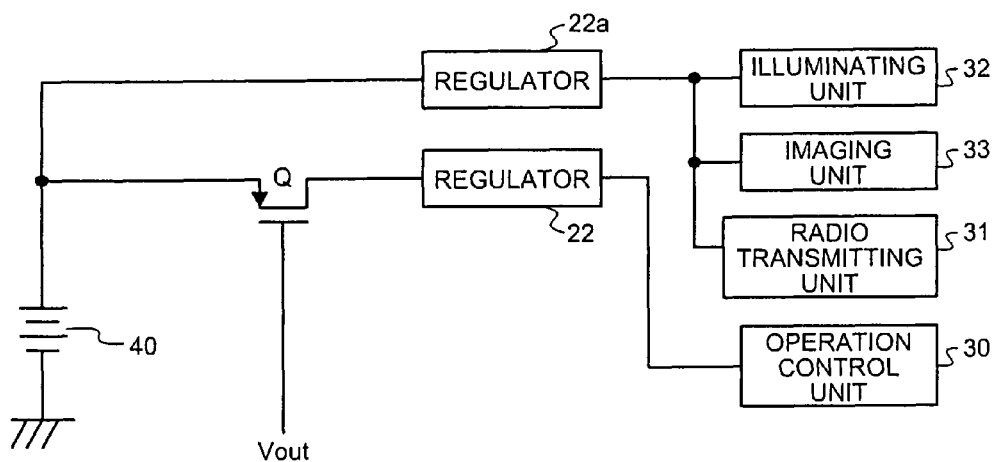
FIG. 6 is a block diagram of a configuration of a power supply system according to a modification of the first embodiment of the present invention.

In FIG. 4, all of the operation control unit 30, the radio transmitting unit 31, the illuminating unit 32, and the imaging unit 33 are subjected to the power supply control according to the on/off of the power supply switch Q. The manner of power supply control is not limited thereto, however. As shown in FIG. 6, another regulator 22a corresponding to the regulator 22 may be additionally arranged. The operation control unit 30 may be connected to the regulator 22, while the illuminating unit 32, the imaging unit 33, and the radio transmitting unit 31 may be connected to the regulator 22a. The power supply switch Q is not provided between the regulator 22a and the battery 40. Only the operation control unit 30 may be subjected to the power supply control according to the on/off of the power supply switch Q. In other words, only a part of the information acquiring unit and the radio transmitting unit of the capsule endoscope 2 may be subjected to the power supply control.

Figure 7:
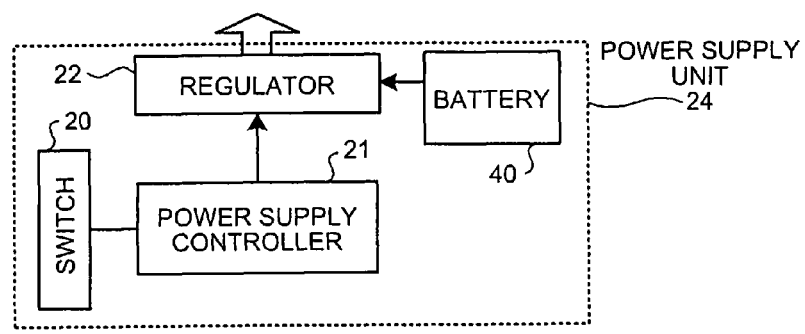
FIG. 7 is a block diagram of a configuration of a power supply unit according to a modification of the first embodiment of the present invention.
Figure 8:
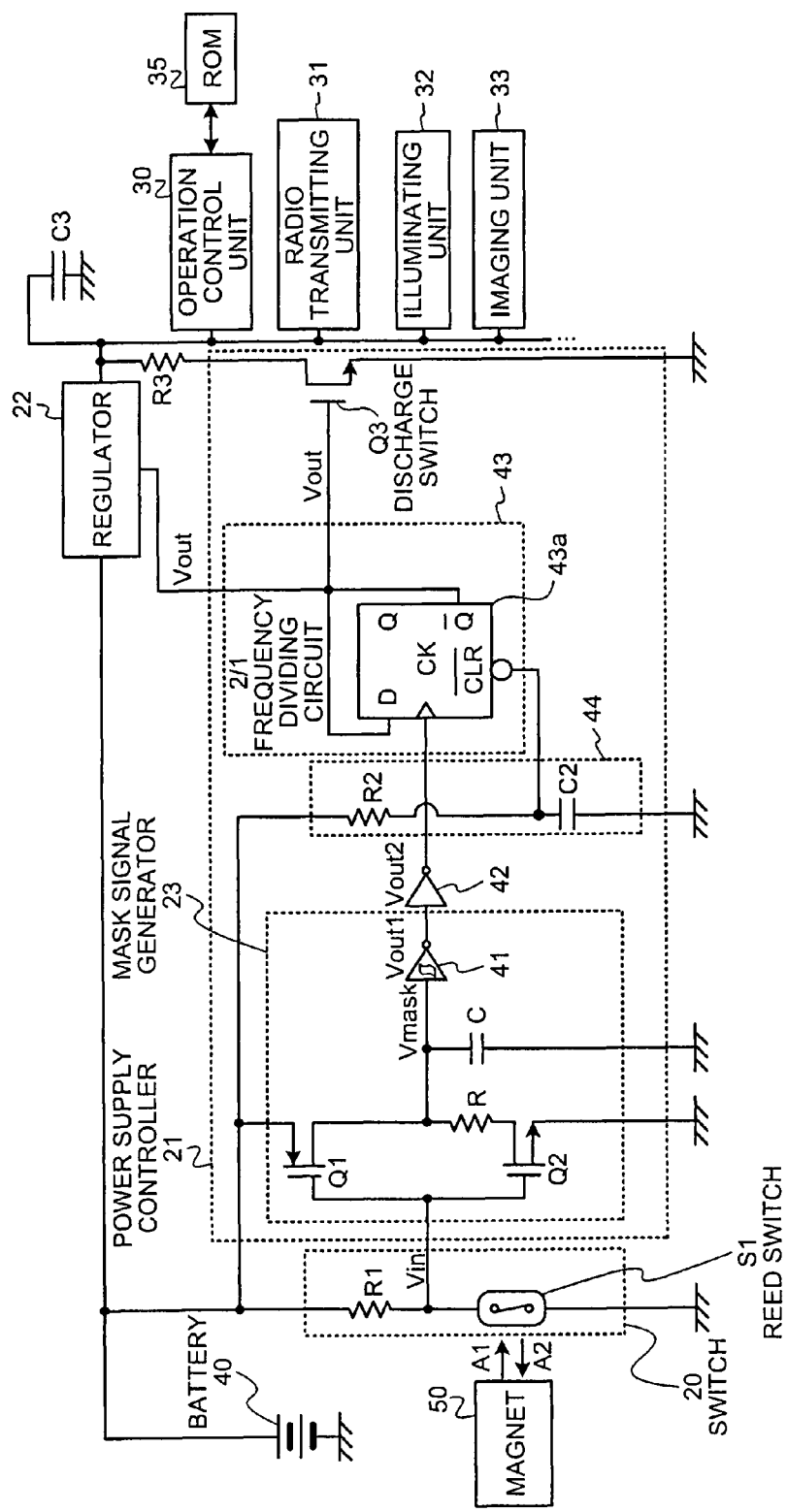
FIG. 8 is a block diagram of a detailed configuration of the power supply unit shown in FIG. 7.

The power supply controller 21 described above performs the power supply control by turning the power supply switch Q on and off. Alternatively, however, the power supply switch Q may be eliminated, and the power supply control may be performed according to the direct switching of the operation mode of the regulator 22 as shown in FIG. 7. Specifically, as shown in FIG. 8, the power supply switch Q may be eliminated, the signal Vout supplied from the ½ frequency dividing circuit 43 may be supplied to the regulator 22, and the regulator 22 may switch over an operation mode in which the power is supplied and a non-operation mode in which the power is not supplied according to the signal Vout. In this case, the power supply unit corresponds to the power supply switch Q and/or the regulator 22.

According to the first embodiment, the initial setting in the power-on time and the reset operation in the power-off time can be stably and securely performed even when the toggle operations for the power on/off are performed repetitiously at high speed. Further, the mask time can be set according to a charge-discharge circuit including the condenser C and the resistor R. Therefore, the stand-by power of the power supply controller 21 during the power-off time can be reduced, whereby the power consumption can be saved. Further, the discharge switch Q3 allows for the discharge of the condenser C3 which is a power supply condenser securely in a short time, whereby the reset operation can be performed even more stably, securely, and speedily.

Second Embodiment

A second embodiment of the present invention will be described. In the first embodiment described above, the minimum mask time is secured with the use of the charge/discharge circuit including the condenser C and the resistor R. In the second embodiment, the minimum mask time is secured with the use of a digital timer.

Figure 9:
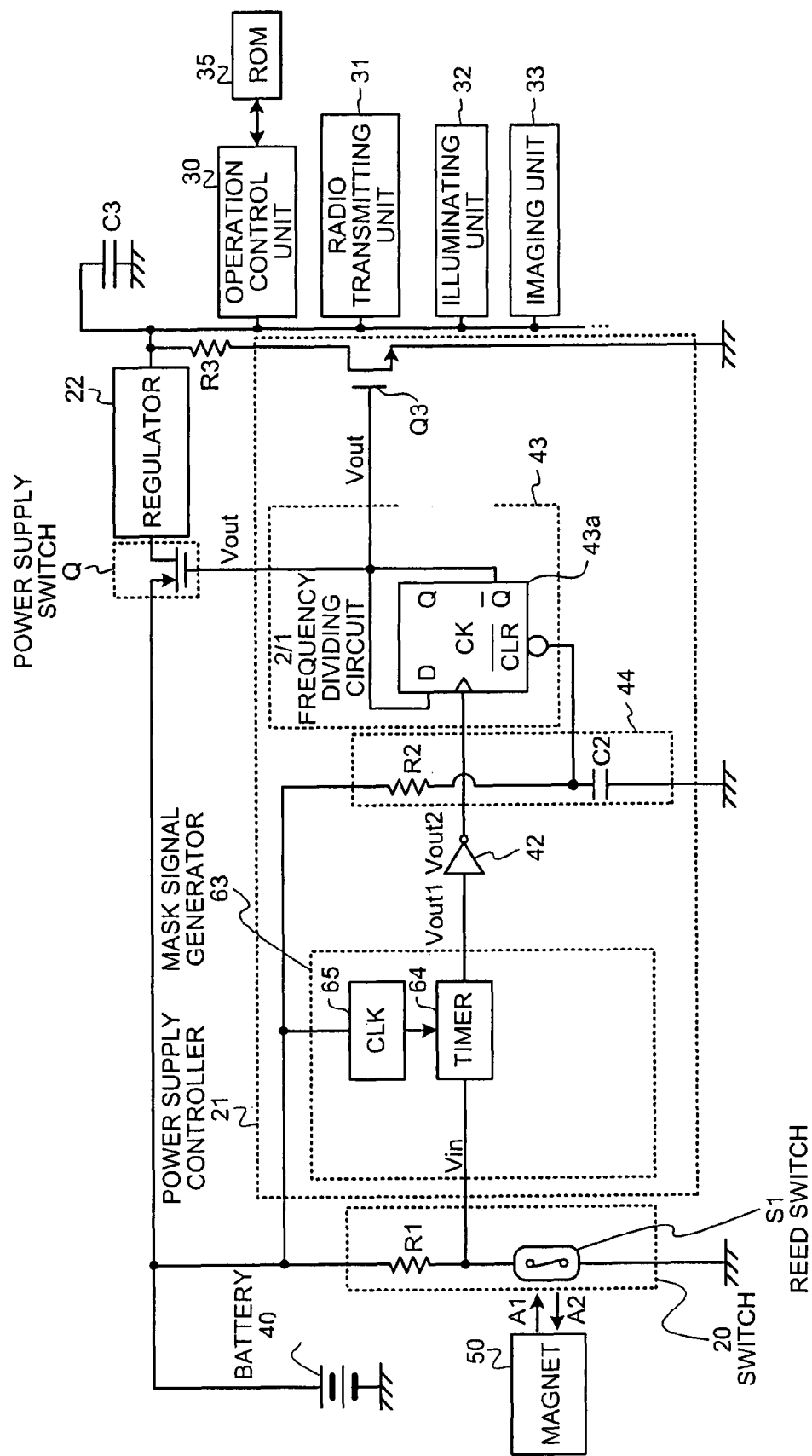
FIG. 9 is a circuit diagram of a detailed configuration of a power supply unit of a capsule endoscope according to a second embodiment of the present invention.
Figure 10:
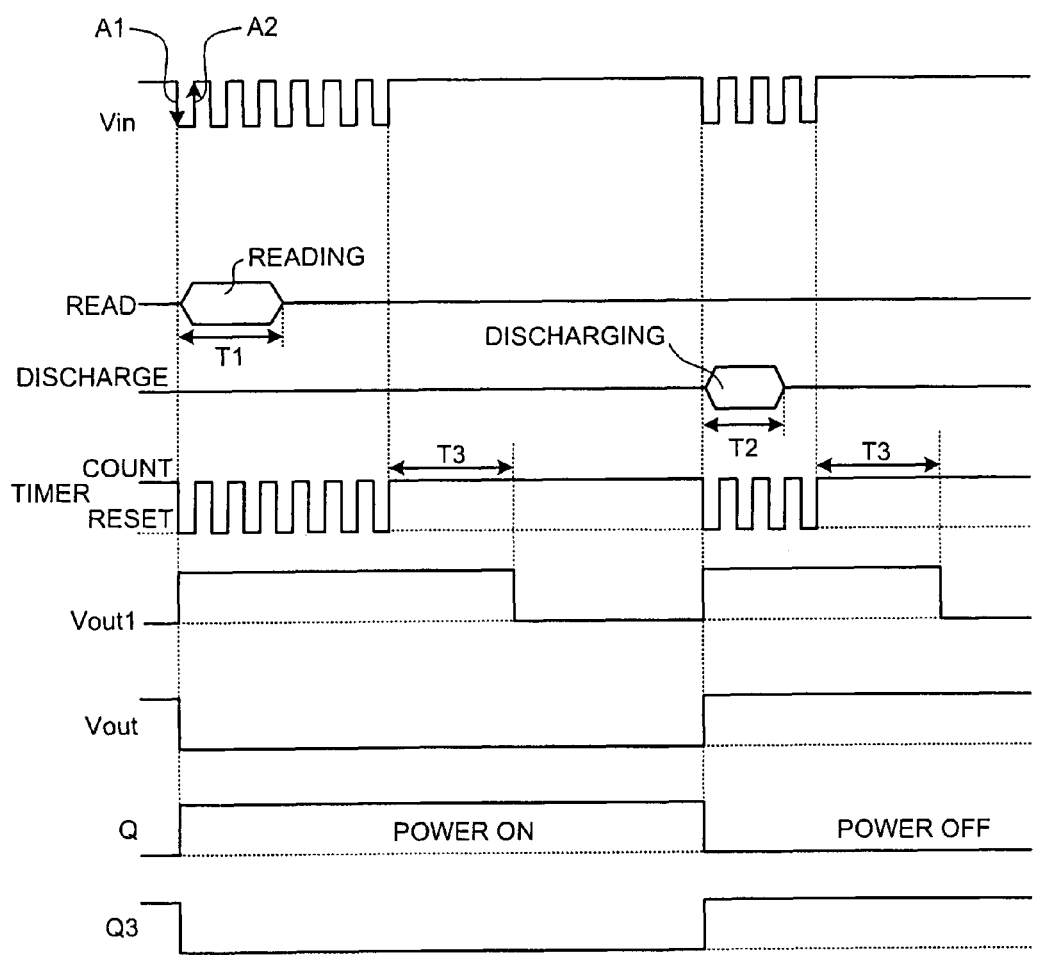
FIG. 10 is a timing chart of operations of a power supply controller shown in FIG. 9.

FIG. 9 shows a detailed configuration of a power supply unit of a capsule endoscope according to the second embodiment of the present invention. FIG. 10 is a timing chart of operations of the power supply unit shown in FIG. 9. In FIGS. 9 and 10, the power supply unit of the second embodiment includes a mask signal generator 63 in place of the mask signal generator 23 shown in relation to the first embodiment. In other respects, the configuration of the second embodiment is the same with that of the first embodiment, and the same element will be denoted by the same reference character.

The mask signal generator 63 includes a clock generator 65 and a timer 64. The clock generator 65 is connected to the battery 40, generates a predetermined clock successively, and supplies the generated clock to the timer 64. The timer 64 receives the signal Vin output from the contact point between the resistor R1 and the reed switch S1, and counts the time according to the clock.

The timer 64 is reset according to the rising of the signal Vin, and turns the signal Vout1 on and supplies to the inverter 42. Further, the timer 64 counts at the falling of the signal Vin. When the counting time exceeds the time T3, the signal Vout1 is turned off and supplied to the inverter 42.

The signal Vout1 which is the same as the signal in the first embodiment can be generated with the use of the timer as described above. Therefore, the same effect and advantage as in the first embodiment can be obtained while the relatively lower power consumption can be realized.

Third Embodiment

A third embodiment of the present invention will be described. In the first and the second embodiments described above, time T1 is secured for the reading processing at the power-on time, and the time T2 is secured for discharge at the power-off time. In the third embodiment, the discharging process is performed at the power-on time, so that the reset-state can be secured at any time.

Figure 11:
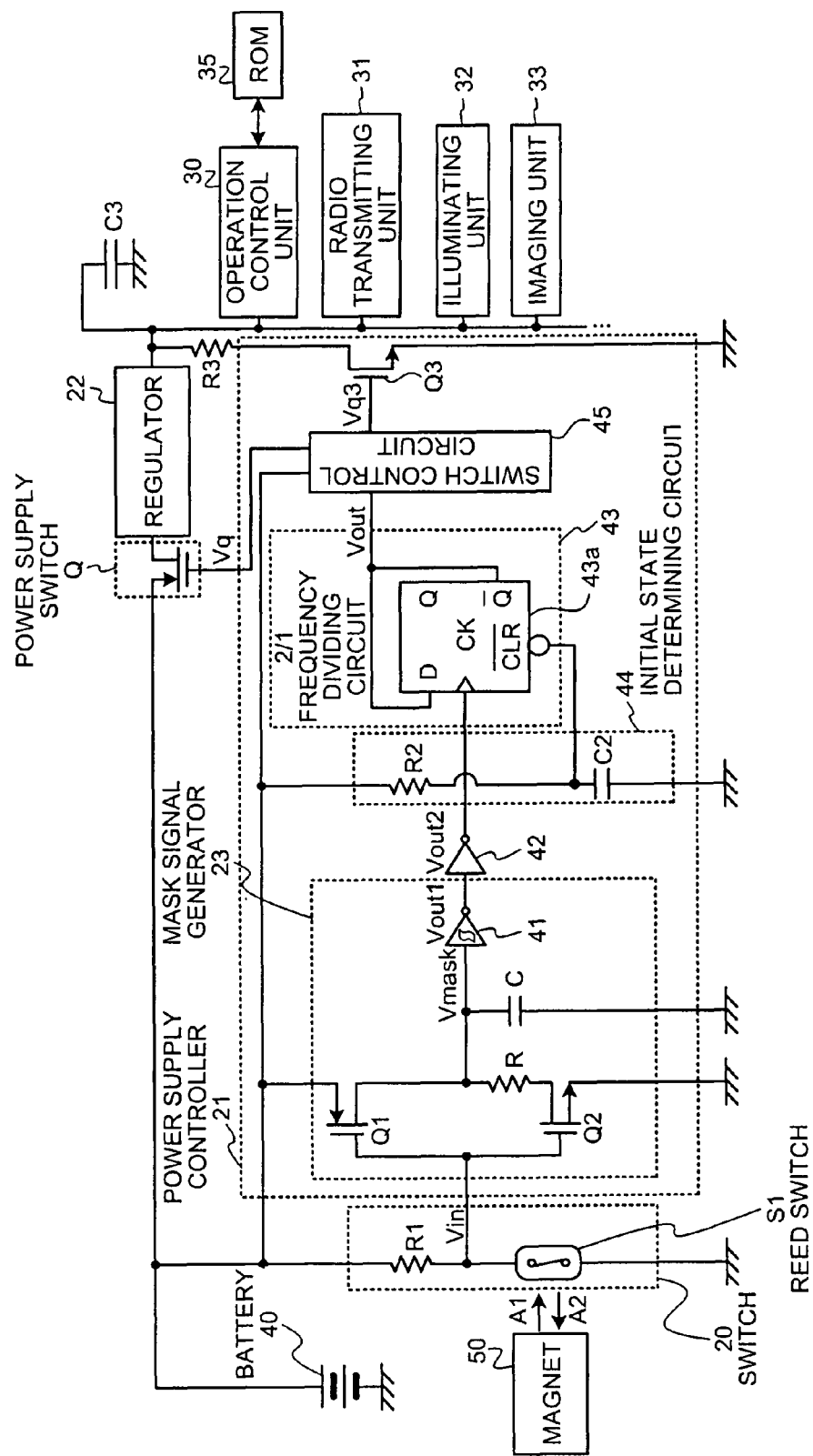
FIG. 11 is a circuit diagram of a detailed configuration of a power supply unit of a capsule endoscope according to a third embodiment of the present invention.
Figure 12:
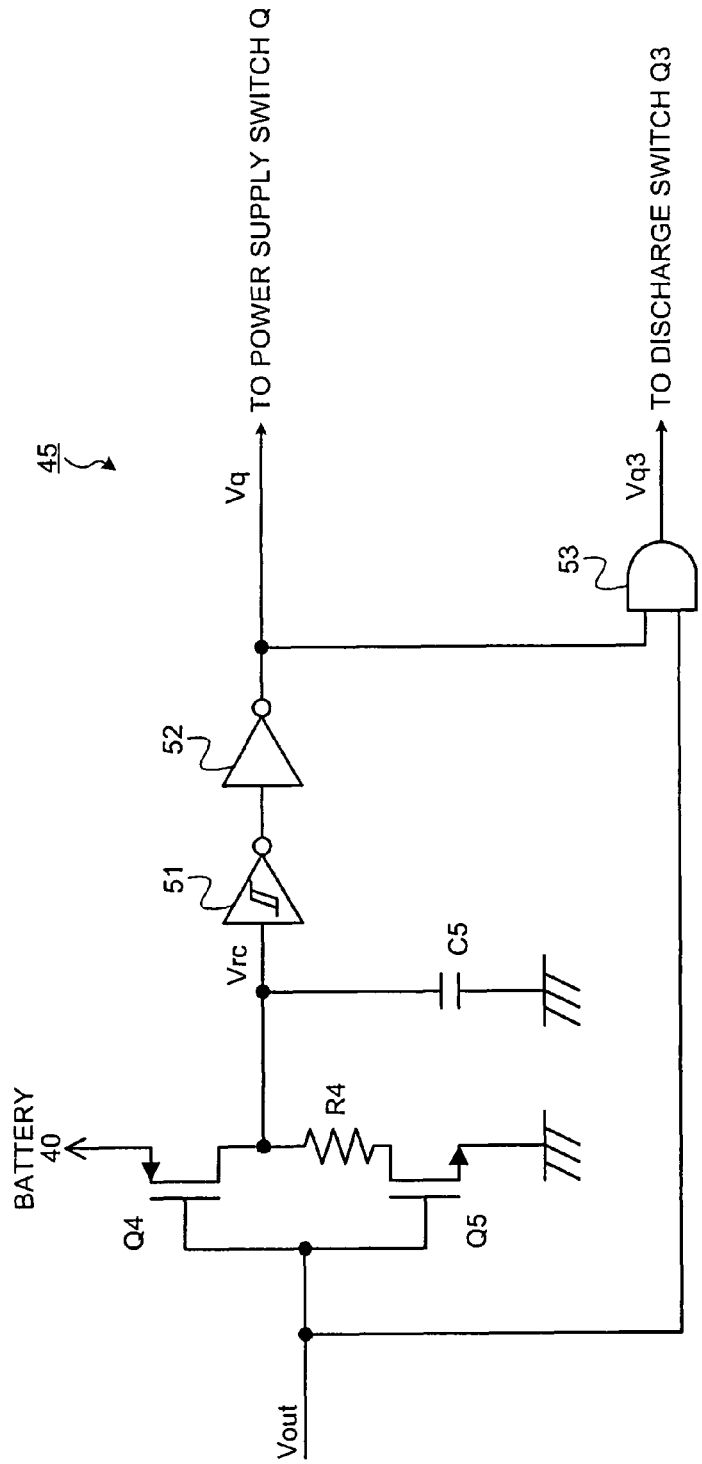
FIG. 12 is a circuit diagram of a detailed configuration of a switch control circuit shown in FIG. 11.
Figure 13:
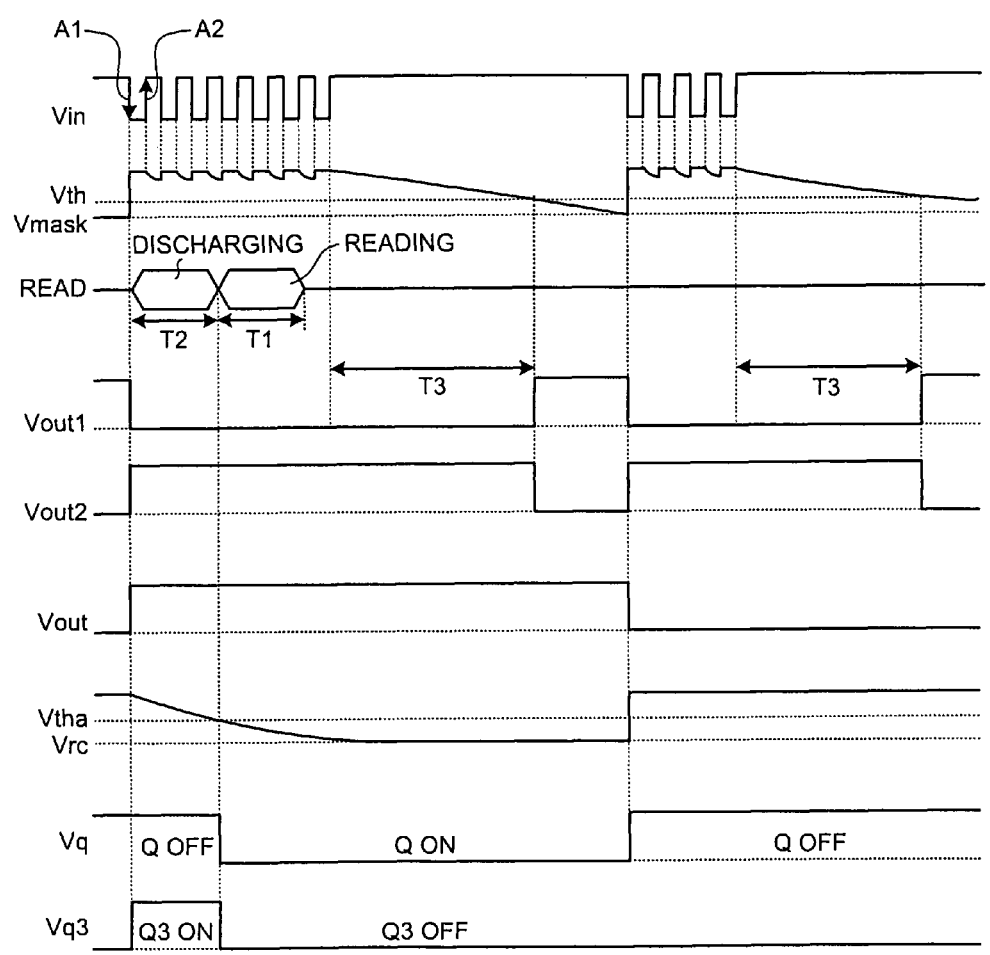
FIG. 13 is a timing chart of operations of a power supply controller shown in FIG. 11.

FIG. 11 shows a detailed configuration of a power supply unit of a capsule endoscope according to the third embodiment of the present invention. FIG. 12 is a circuit diagram of a detailed configuration of a switch control circuit shown in FIG. 11. FIG. 13 is a timing chart of operations of the power supply unit shown in FIG. 11. In FIG. 11, the power supply unit of the third embodiment further includes a switch control circuit 45 within the power supply unit shown in the first embodiment. In other respects, the configuration of the third embodiment is the same as that of the first embodiment, and the same element is denoted by the same reference character.

The switch control circuit 45 is arranged at a subsequent stage of the ½ frequency dividing circuit 43. Using the signal Vout (Q output) supplied from the ½ frequency dividing circuit 43, the switch control circuit 45 generates and outputs a signal Vq for controlling the power supply switch Q and a signal Vq3 for controlling the discharge switch Q3. As shown in FIG. 13, the switch control circuit 45 controls so that the discharge switch Q3 is turned to an on-state to discharge before the reading at the power-on time, and so that the power supply switch Q is turned on to perform reading after the discharge is finished.

As shown in FIGS. 12 and 13, the switch control circuit 45 receives the signal Vout (Q output) supplied from the ½ frequency dividing circuit 43. The switch control circuit 45, similarly to the mask signal generator 23, includes a complementary switching circuit including a p-MOS transistor Q4 and an n-MOS transistor Q5. Each of the gates of the p-MOS transistor Q4 and the n-MOS transistor Q5 receives the signal Vout. The source of the p-MOS transistor Q4 is connected to the battery 40, and the drain thereof is connected to the source of the n-MOS transistor Q5 via a resistor R4. The drain of the n-MOS transistor Q5 is grounded. Further, a condenser C5 is connected to a side of the resistor R4 connected to the drain of the p-MOS transistor Q4. The other side of the condenser C5 is grounded. A signal Vrc output from one end of the condenser C5 is supplied to an inverter 51, which outputs a signal of the ground level when the Vrc exceeds a predetermined threshold Vtha, and outputs the signal of the power supply level when the Vrc is equal to or lower than the threshold Vtha. Further, an inverter 52 is connected to a subsequent stage of the inverter 51. The inverter 52 outputs the signal Vq for controlling the power supply switch Q. At the same time, the signal Vout and the signal Vq are supplied to an AND circuit 53, which performs an AND operation of the signal Vout and the signal Vq to obtain the signal Vq3, which is output as a signal for controlling the discharge switch Q3.

The condenser C5 and the resistor R4 are set so that the discharge voltage determined by the time constant of the condenser C5 and the resistor R4 attains the threshold Vtha after the discharge time T2 elapses. During the discharge time T2, the signal Vq is at the power supply level, and the power supply switch Q is in an off-state. The signal Vq3 is at the power supply level and the discharge switch Q3 is in an on-state. After the time T2, the signal Vq attains a ground level and the power supply control switch Q attains an on-state, while the signal Vq3 attains the ground level and the discharge switch Q3 attains an off-state. In other words, during the discharge time T2 before the power supply switch Q attains an on-state, the switching control is performed for the power-off state and the discharge state, so that the transition to the power-on state is delayed. At the power-off time, the discharge processing is not performed. This is because at the next transition to the power-on state, the discharge processing is performed first. Further, the time T3 in the third embodiment is a time exceeding the sum of the discharge time T2 and the reading time T1.

The switch control circuit 45 can be applied to the second embodiment. The switch control circuit 45 may be arranged at a subsequent stage of the ½ frequency dividing circuit 43 shown in FIG. 9, and generates and outputs the signal Vq and the signal Vq3 using the signal Vout output from the ½ frequency dividing circuit 43.

In the third embodiment, since the switch control circuit 45 is provided to discharge electric charges in the condenser C3 at the initial stage of the power-on time, the reset operation can be performed securely.

In the first to the third embodiments described above, the combination of the magnet 50 and the reed switch S1 is described. The present invention, however, is not limited thereto, and can be similarly applied to an apparatus using other detecting circuit that detects control signals transmitted by radio such as light including infrared light, and electromagnetic waves.

Further, the in-vivo information described in the first to the third embodiments includes, other than the in-vivo image information obtained through image-pickup by the imaging unit 33, information acquired by the sensor unit 34 inside the living body, such as temperature information, pressure information, pH information, and position information.

Further, though the in-vivo information is transmitted by radio by the radio transmitting unit 31 in the first to the third embodiments, it is possible to arrange a unit that induces electric field in an electric-field transmitting medium inside the living body in place of the radio transmitting unit 31, and to transmit the in-vivo information to the outside of the subject 1 by a living-body communication in which the in-vivo information is transmitted via the electric-field transmitting medium.

Further, though the discharge switch Q3 is realized with a semiconductor switch such as an n-MOS transistor in the first to the third embodiments, the discharge switch Q3 may be a mechanical switch.

Further, though the toggle operations are realized with the ½ frequency dividing circuit 43 in the first to the third embodiments, the ½ frequency dividing circuit 43 may be eliminated and the power supply switch Q may be turned on and off corresponding to the on/off operations of the reed switch S1. In this case, the mask signal generators 23 and 63 can lengthen the pulse width of the reed switch S1 by the time T3, so that the reading time and the discharge time can be secured.

Further, though the on/off operations of the power supply switch Q is controlled by a single switch, i.e., the reed switch S1 in the first to the third embodiments, the on operation and the off operation of the power supply switch Q may be controlled by different switches. For example, the reed switch may be employed for the on operation, and a light detecting switch may be employed for the off operation. Alternatively, a single light detecting switch may be employed, and different codes may be used for a light control signal at the on-operation time and for a light control signal at the off-operation time. In these cases, the mask signal generator is also provided, so that the pulse width is lengthened by the time T3, whereby the reading time and the discharge time can be secured.

In the in-vivo information acquiring apparatus according to the present invention, the masking unit can perform a masking of a control signal supplied from the external signal detecting unit to the switch control unit for a predetermined time period using the charge/discharge circuit and the like. Therefore, the power control can be performed so that the reset operation can be securely performed with low power consumption.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

The in-vivo information acquiring apparatus according to the present invention as described above is useful for the acquisition of various types of in-vivo information such as image information, temperature information, and pH information of the inside of the subject, and particularly suitable for the in-vivo information acquiring apparatus, that can perform the power supply control so as to allow for the secure reset operation of an internal circuit with a low power consumption.

What is claimed is:

1. An in-vivo information acquiring apparatus comprising:
   an information acquiring unit that acquires in-vivo information;
   a transmitting unit that transmits the in-vivo information to an outside of a living body;
   a power source that serves to supply power to the information acquiring unit and the transmitting unit;
   a power supply unit that is provided between the power source and at least one of the information acquiring unit and the transmitting unit so as to supply the power of the power source to at least one of the information acquiring unit and the transmitting unit;
   an external signal detecting unit that detects an external control signal supplied from outside and generates a control signal according to a detected state of the external control signal;
   a power supply controller that controls a power supply state of the power supply unit according to the control signal supplied from the external signal detecting unit; and
   a masking unit that masks the control signal supplied to the power supply controller by the external signal detecting unit for a predetermined time period, wherein the masking unit is a pulse-width extending circuit that prolongs a pulse width of the control signal for the predetermined time period.

2. The in-vivo information acquiring apparatus according to claim 1, wherein
   the pulse-width extending circuit includes a charge/discharge circuit.

3. The in-vivo information acquiring apparatus according to claim 1, wherein
   the pulse-width extending circuit includes a timer.

4. The in-vivo information acquiring apparatus according to claim 1, further comprising
   a discharging unit that discharges electric charges of a condenser connected to the power supply unit, wherein
   the discharging unit starts discharging substantially at the same timing as a stopping of power supply by the power supply controller.

5. The in-vivo information acquiring apparatus according to claim 1, further comprising
   a discharging unit that discharges electric charges of a condenser connected to the power supply unit, wherein
   the discharging unit starts discharging at timing before the starting of power supply by the power supply controller.

6. The in-vivo information acquiring apparatus according to claim 4, wherein
   the discharging unit includes a semiconductor switch.

7. The in-vivo information acquiring apparatus according to claim 4, wherein
   the discharging unit includes a mechanical switch.

8. The in-vivo information acquiring apparatus according to claim 1, wherein
   the predetermined time period is a time exceeding an initial setting time of at least one of the information acquiring unit and the transmitting unit at a time of power supply by the power supply unit.

9. The in-vivo information acquiring apparatus according to claim 1, wherein
   the predetermined time period is a time exceeding a time required for at least one of the information acquiring unit and the transmitting unit to lower to a resettable voltage when the power supply by the power supply unit is stopped.

10. The in-vivo information acquiring apparatus according to claim 1, wherein
the predetermined time period is a time exceeding a sum of an initial setting time of at least one of the information acquiring unit and the transmitting unit and a time required for at least one of the information acquiring unit and the transmitting unit to lower to a resettable voltage at a time of power supply by the power supply unit.

11. The in-vivo information acquiring apparatus according to claim 1, wherein
the power supply controller performs a toggle operation of a power-supply state and a power-supply suspension state of the power supply unit according to the control signals supplied from the external signal detecting unit.

12. The in-vivo information acquiring apparatus according to claim 1, wherein
plural external control signals are supplied from the outside, and
different external control signals are employed at a power supply time and a power supply suspension time of the power supply unit.

13. The in-vivo information acquiring apparatus according to claim 1, wherein
the external control signal is one of a magnetic signal, an optical signal, and a radio signal, or a combination of any of them.

14. The in-vivo information acquiring apparatus according to claim 1, wherein
the in-vivo information is one of in-vivo image information, temperature information, pressure information, pH information, and position information, or a combination of any of them.

15. The in-vivo information acquiring apparatus according to claim 1, wherein
the transmitting unit is a radio communication unit.

16. The in-vivo information acquiring apparatus according to claim 1, wherein
the transmitting unit is a living-body communication unit.

* * * * *